(12) United States Patent  
Ozaki (10) Patent No.: US 8,511,826 B2  
(45) Date of Patent: Aug. 20, 2013

(54) OPTOMETRIC APPARATUS

(75) Inventor: Yoshihiro Ozaki, Aichi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 13/273,307

(22) Filed: Oct. 14, 2011

(65) Prior Publication Data

US 2012/0092621 A1 Apr. 19, 2012

(30) Foreign Application Priority Data

Oct. 15, 2010 (JP) .................................. 2010-232936

(51) Int. Cl.
*A61B 3/02* (2006.01)

(52) U.S. Cl.
USPC .............................. 351/239; 351/234; 351/222

(58) Field of Classification Search
USPC ................... 351/200, 222, 233, 234, 235, 239
See application file for complete search history.

(56) References Cited

U.S. PATENT DOCUMENTS 6,033,076 A * 3/2000 Braeuning et al. ............ 351/224  
6,048,064 A * 4/2000 Hosoi et al. .................... 351/212

FOREIGN PATENT DOCUMENTS

JP 11-019041 A 1/1999  
JP 2007-068574 A 3/2007

* cited by examiner

*Primary Examiner* — Darryl J Collins  
*Assistant Examiner* — Gary O'Neill  
(74) *Attorney, Agent, or Firm* — Lowe Hauptman Ham & Berner, LLP (57) ABSTRACT

An optometric apparatus for examining visual functions of an examinee's eye includes: a memory for storing prism powers corresponding to the visual functions of the examinee's eye; an output unit; and a control unit for graphically displaying on the output unit normative areas being areas of normative prism powers in addition to information on prism powers of the examinee's eye based on the prism powers stored in the memory.

16 Claims, 6 Drawing Sheets

OPTOMETRIC APPARATUS

CROSS-REFERENCE TO RELATED APPLICATION

This application is based on Japanese Patent Application No. 2010-232936 filed with the Japan Patent Office on Oct. 15, 2010, the entire content of which is hereby incorporated by reference.

BACKGROUND

1. Technical Field

The present disclosure relates to an optometric apparatus for subjectively examining (measuring) the visual functions of an examinee's eye.

2. Related Art

A subjective-type optometric apparatus (phoropter or refractor) having a pair of right and left lens chamber units with a test window has been known. This apparatus is disclosed in, for example, JP-A-11-19041 (U.S. Pat. No. 6,048,064). When a refractive error of an examinee's eye is corrected, an accurate examination (a perfectly corrected refractive power test) is conducted for a refractive state of the examinee's eye. In consideration of the powers of former spectacles (or former contact lenses), the complaints of the examinee, and the like, prescription powers of new spectacles (or contact lenses), which provide them with comfortable wearing without fatigue, are determined. In other words, first, responses on appearances of a presented test chart are obtained from the examinee in the perfectly corrected refractive power test. Consequently, perfect correction powers in which the best visual acuity can be obtained are found. Prescription powers are then obtained based on these powers and the like.

In addition, if the examinee's eye suffers a visual dysfunction such as phoria, the visual dysfunction is properly analyzed and corrected. In the apparatus in JP-A-11-19041 (U.S. Pat. No. 6,048,064), a horizontal phoria test, a vertical phoria test, a divergence test (a negative relative vergence test), and a convergence test (a positive relative vergence test), and the like are conducted on the examinee's eye, and the test results (analysis results) are displayed. Based on the display, the examiner calculates prescription values (prescription powers) to correct the visual dysfunction.

SUMMARY

An optometric apparatus for examining visual functions of an examinee's eye includes: a memory for storing prism powers corresponding to the visual functions of the examinee's eye; an output unit; and a control unit for graphically displaying on the output unit normative areas being areas of normative prism powers in addition to information on prism powers of the examinee's eye based on the prism powers stored in the memory.

DETAILED DESCRIPTION

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically illustrated in order to simplify the drawing.

Test results about the amount of phoria and the like of an examinee's eye cannot be easily recognized. The display disclosed in JP-A-11-19041 (U.S. Pat. No. 6,048,064) is difficult for an inexperienced examiner to understand.

A technical object of the present disclosure is to provide an optometric apparatus that enables an examiner to easily grasp the analysis results of binocular visual function tests such as a phoria test and to easily obtain an appropriate prescription value.

An optometric apparatus of the embodiment includes the following configuration.

An optometric apparatus for examining visual functions of an examinee's eye includes: a memory for storing prism powers corresponding to the visual functions of the examinee's eye; an output unit; and a control unit for graphically displaying on the output unit normative areas being areas of normative prism powers in addition to information on prism powers of the examinee's eye based on the prism powers stored in the memory.

The optometric apparatus enables an examiner to easily grasp the analysis results of binocular visual function tests such as a phoria test and easily obtain an appropriate prescription value.

Figure 1:
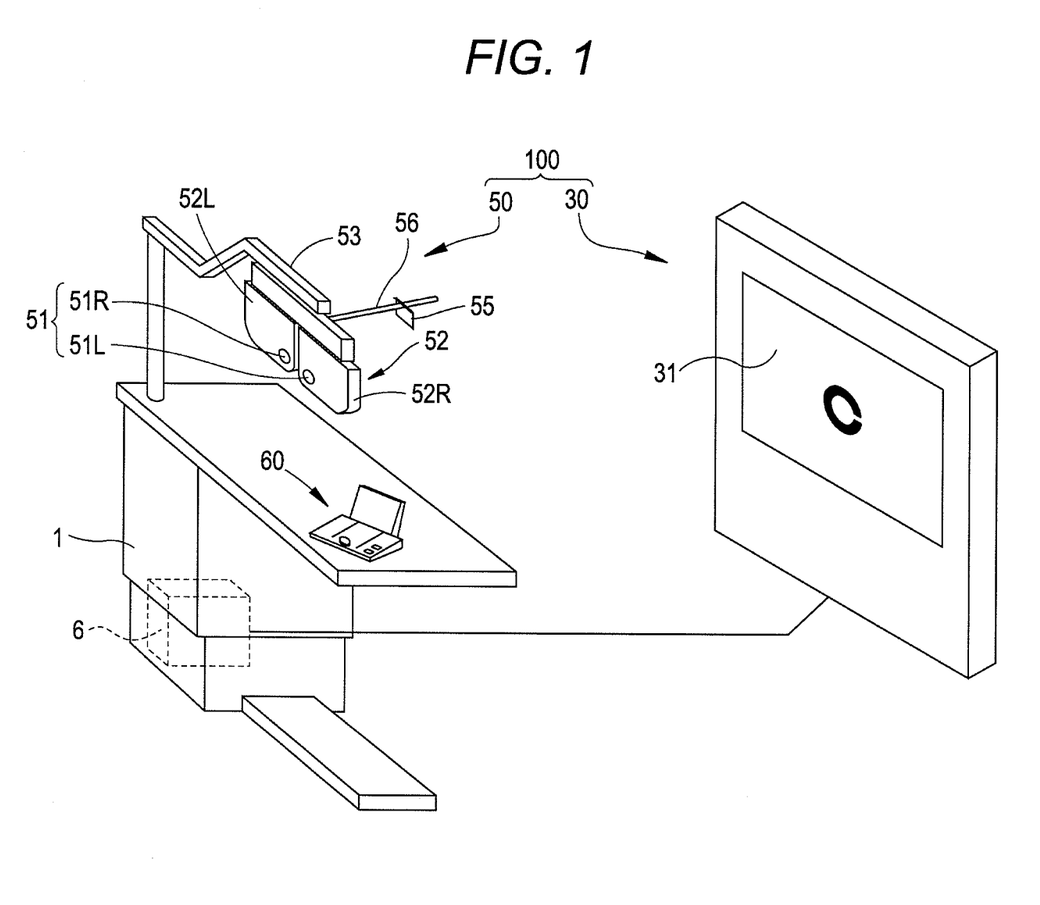
FIG. 1 is a schematic diagram illustrating a configuration of an optometric system.

A description will hereinafter be given of an optometric system according to the embodiment based on the drawings. FIG. 1 is a schematic diagram illustrating a configuration of an optometric system 100. The optometric system 100 mainly includes an optometric apparatus 50 and a chart presenting apparatus 30. The optometric apparatus 50 subjectively examines the visual functions of an examinee's eye. The chart presenting apparatus 30 presents a distance test chart to the examinee's eye. The optometric apparatus 50 is fixed to an optometric table 1. The optometric apparatus 50 has a pair of lens chamber units 52 (a left lens chamber unit 52L and a right lens chamber unit 52R) and a support unit 53. The shapes of the left lens chamber unit 52L and the right lens chamber unit 52R are bilaterally symmetric. The support unit 53 supports the lens chamber unit 52 while hanging it down therefrom.

Lens disks are rotatably held in the lens chamber unit 52. Multiple optical elements such as a spherical lens, a cylindrical lens, a dispersion prism, and a rotary prism are disposed in the lens disks on the same circumference. Any of these optical elements is disposed in a test window 51 (a left test window 51L and a right test window 51R) formed in the lens chamber unit 52. The switching or the like of the optical element disposed in the test window 51 is performed by operating a controller 60 being an input unit (operation unit). The support unit 53 has a space adjustment mechanism (including a convergence mechanism) of the lens chamber unit 52. The space adjustment mechanism adjusts the space between the left test window 51L and the right test window 51R in accordance with the pupillary distance of the examinee. Moreover, a near-point rod 56 is fixed to an approximately middle section of the support unit 53 (in the vicinity of the midpoint between the left lens chamber unit 52L and the right lens chamber unit 52R). The near-point rod 56 slidably holds a chart presenting unit (near test chart presenting unit) 55. The chart presenting unit 55 is moved to keep a distance of 20 to 70 cm from the test window 51. In the embodiment, the distance between the chart presenting unit 55 and the test window 51 is set at 40 cm in a near visual acuity value test or a near binocular visual function test.

The chart presenting apparatus 30 has a display (chart presenting unit) 31 for presenting a distance test chart. The chart presenting apparatus 30 is connected to the controller 60 via a relay unit 6. The switching or the like of a chart displayed on the display 31 is performed by operating the controller 60. The controller 60 is provided with various switches such as a switch for conducting visual acuity value tests and a switch for conducting binocular visual function tests. The chart presenting apparatus 30 presents (displays) any one of a distance visual acuity value test chart and a distance binocular visual function test chart on the display 31 in accordance with the operation of the switch. The chart presenting apparatus 30 is installed at approximately the same height as the optometric apparatus 50. Moreover, the chart presenting apparatus 30 is placed at a distance appropriate for testing from the optometric apparatus 50. In the embodiment, the distance (test distance or installation distance) between the optometric apparatus 50 and the chart presenting apparatus 30 is set at a distance appropriate for a far test, for example, 5 m.

Figure 2:
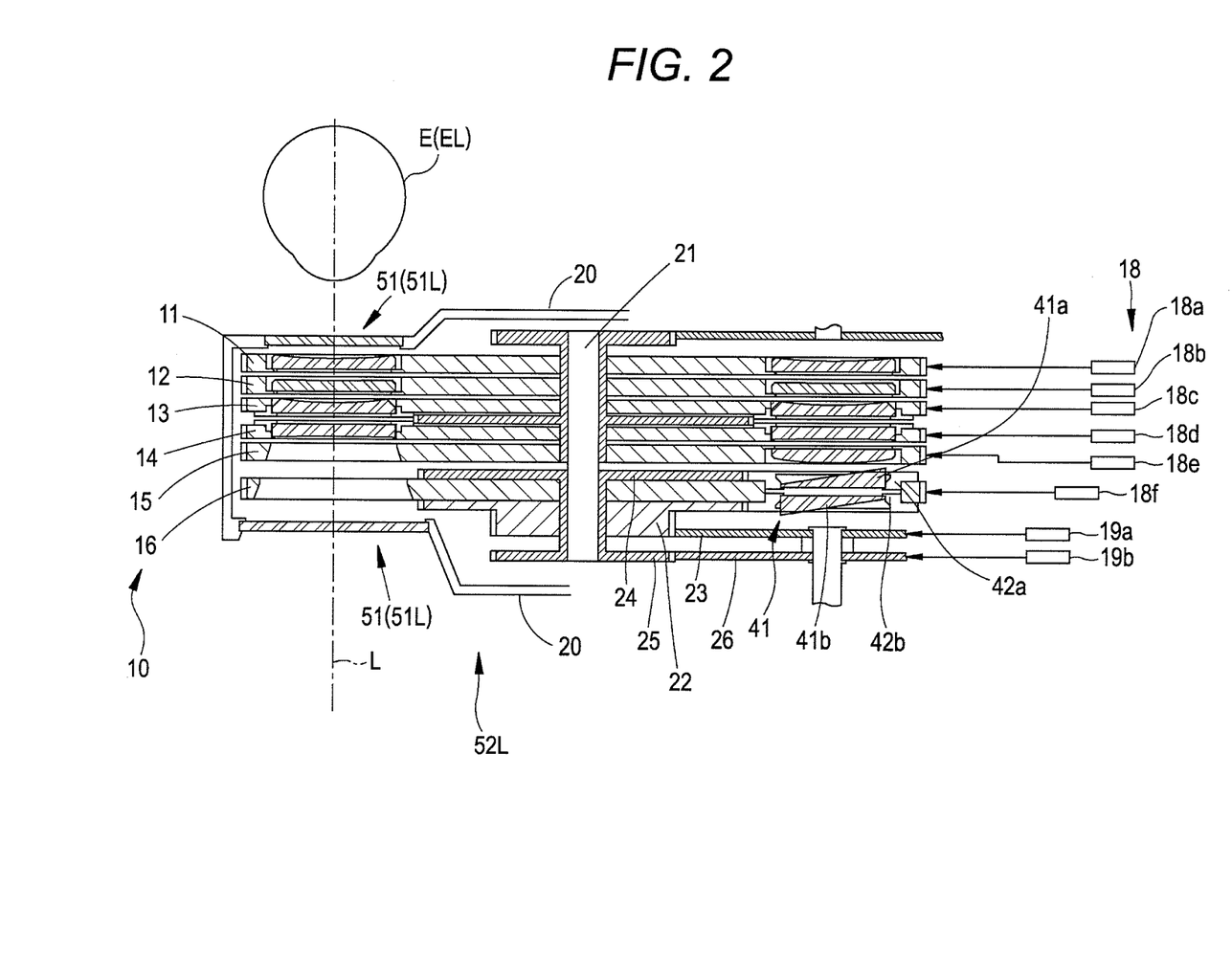
FIG. 2 is a view illustrating a configuration of a lens chamber unit of an optometric apparatus.

FIG. 2 is a partial sectional view where the cross section of the left lens chamber unit 52L for examining the left eye is viewed from above. Upon testing, an examinee's eye E (a left eye EL) is positioned on a measurement optical axis L. A group of lens disks 10 are disposed in a cover 20 of the lens chamber unit 52. Six lens disks 11 to 16 are disposed in the group of lens disks 10 with a shaft 21 as a rotational center. The lens disks 11 to 16 include an open aperture (or a lens of 0 D) and a plurality of optical elements. The strong spherical lens disk 11, the weak spherical lens disk 12, the strong cylindrical lens disk 13, the weak cylindrical lens disk 14, the first auxiliary lens disk 15, and the second auxiliary lens disk 16 are disposed in this order from the examinee's eye E. Gears are formed on the rim of the lens disks 11 to 16. The lens disks 11 to 16 are meshed with corresponding pinion gears. These pinion gears are attached to rotation shafts of corresponding motors 18 (motors 18a to 18f). The motors 18 (the motors 18a to 18f) rotate the group of lens disks 10 (the lens disks 11 to 16). As a result, the optical elements disposed on the optical axis L can be switched. Incidentally, protective covers are attached to the test window 51 (51L) from both the examiner's side and the examinee's side, respectively. Incidentally, the number of lens disks is not limited to six. The number of lens disks may be arbitrarily determined depending on the type and number of optical elements such as lenses to be used.

The lens disks 11 and 12 hold spherical lenses. The open apertures (or the lenses of 0 D) and a plurality of spherical lenses with different powers are disposed (provided) in the lens disks 11 and 12. The lens disks 13 and 14 hold cylindrical lenses. The open apertures (or the lenses of 0 D) and a plurality of cylindrical lenses with different powers are disposed (provided) in the lens disks 13 and 14. Incidentally, the cylindrical lenses of the lens disks 13 and 14 are rotatable around the optical axis L.

The lens disk 15 holds a first group of auxiliary lenses. Other than the open aperture (or the lens of 0 D), a spherical lens of +0.12 D, red/green filters, a dispersion prism (6/10 Δ), a cross cylinder lens of ±0.50 D, polarizing plates (135° and 45°), a polarizing plate with +0.12 D, a maddox lens, and the like are disposed (provided) in the lens disk 15 as the first group of auxiliary lenses. Incidentally, the first group of auxiliary lenses is not limited to them.

The lens disk 16 holds a second group of auxiliary lenses. Other than the open aperture (or the lens of 0 D), a rotary prism 41, cross cylinder lenses (of ±0.25 D and ±0.50 D), an auto-cross cylinder lens of ±0.25 D, a plain lens with marks for interpupillary adjustment, a spherical lens of +10 D, a spherical lens of −10 D, and the like are disposed (provided) in the lens disk 16 as the second group of auxiliary lenses. Incidentally, the rotary prism 41 and the cross cylinder lenses are rotatable around the optical axis L. Moreover, the second group of auxiliary lenses is not limited to them.

The rotary prism 41 has two prisms 41a and 41b of the same power. The rotary prism 41 continuously changes the prism power and the base direction by relatively rotating the prisms 41a and 41b.

The prisms 41a and 41b are attached to the disk 16 by holders 42a and 42b where gears are formed. The prisms 41a and 41b are rotatable around the optical axis L. The gear of the holder 42a is meshed with a large gear 22 that rotates around the shaft 21. A gear integrally formed inside the large gear 22 is coupled, via a relay gear 23, to a pinion gear attached to a rotation shaft of a motor 19a. The rotation of the motor 19a is transferred to the holder 42a via the gears 23 and 22. On the other hand, the gear of the holder 42b is meshed with a large gear 24 that rotates around the shaft 21. A gear 25 fixed to the large gear 24 is coupled, via a relay gear 26, to a pinion gear attached to a rotation shaft of a motor 19b. The rotation of the motor 19b is transferred to the holder 42b via the gears 26, 25 and 24. In this manner, the prism 41a is rotated by driving the motor 19a. Furthermore, the prism 41b is rotated by driving the motor 19b. Consequently, the prisms 41a and 41b are rotated independently of each other. As a result, the prisms 41a and 41b are disposed in the test window 51 positioned in front of the examinee's eye in a desired condition.

Furthermore, the rotational mechanism of the cylindrical lens and the rotational mechanism of the cross cylinder lens are similar to the rotational mechanism of the rotary prism 41. Moreover, the technology disclosed in JP-A-2007-68574 can be used for the rotational mechanism of the cylindrical lens, the rotational mechanism of the rotary prism 41, and the like.

Figure 3:
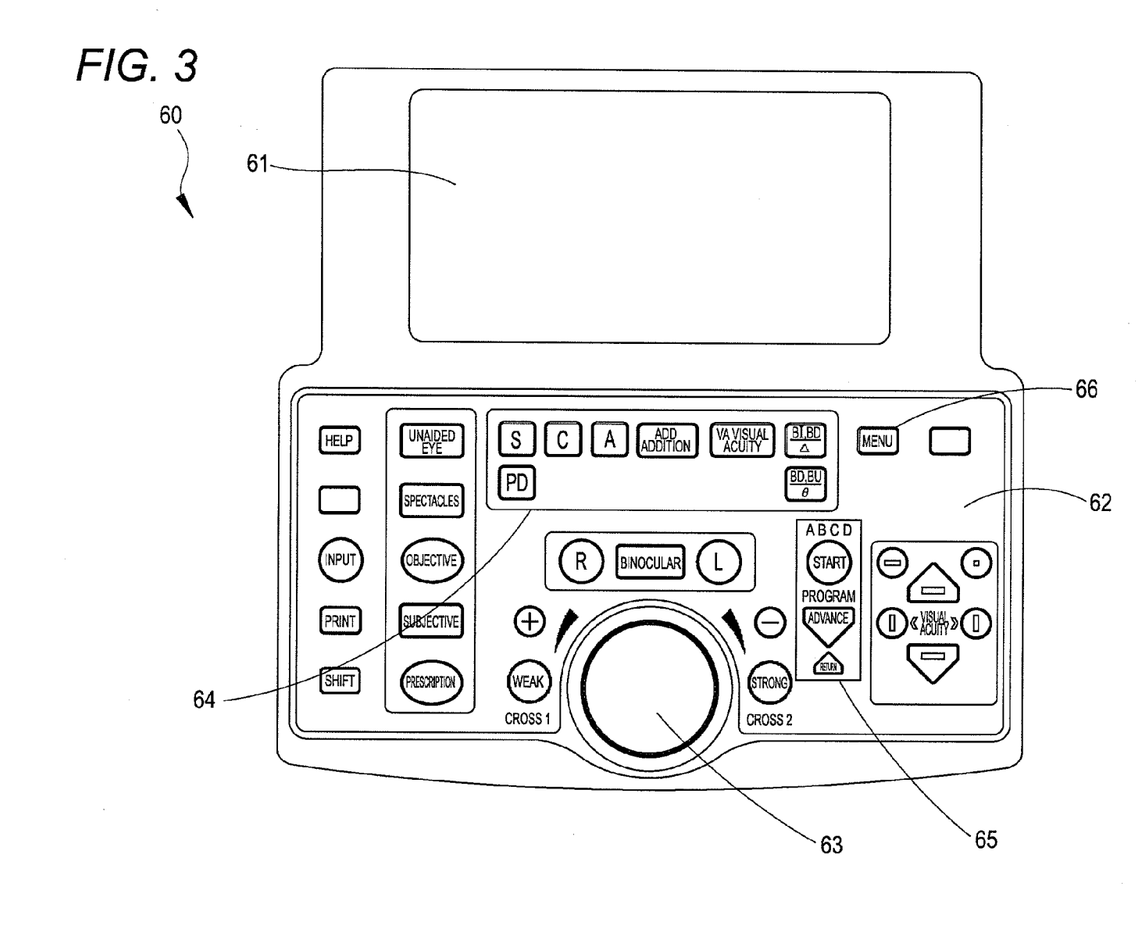
FIG. 3 is a view illustrating a configuration of a controller of the optometric apparatus.

Next, a description will be given of the controller 60 in the embodiment. FIG. 3 is an external view where the controller 60 is viewed from above. The controller 60 includes a monitor 61, a switch panel 62, and the like. The monitor 61 functions as a display unit (an output unit) and an input unit (an operation unit). The display unit displays a chart, a test content, a test result, and the like, which are presented to the examinee. A plurality of switches of various types being input units (operation units) is disposed on the switch panel 62. The monitor 61 is a color display having a touch panel function. The examiner can operate the optometric apparatus 50 (or the optometric system 100) by selecting (touching) a chart, test items, and the like, which are displayed on the monitor 61. A dial switch 63, a mode switch 64, a start/advance switch 65 for a program test, a menu switch 66, and the like are provided on the switch panel 62. The dial switch 63 is a switch for inputting signals for increasing and decreasing numerical values, switching the optical element, and the like by being turned to the right and left. The mode switch 64 is a switch for switching a mode that changes data such as a spherical dioptic power S, an astigmatic power C, an astigmatic axis angle A, and a pupillary distance PD. The menu switch 66 is a switch for setting or changing a display mode. For example, the dial switch 63 is rotated in a horizontal phoria test. Consequently, the prism power Δ of the rotary prism 41 disposed in the test window 51 is increased and decreased. If the dial switch 63 is rotated to the right, the rotary prism 41 is rotated to increase the prism power in an inward direction. On the other hand, if the dial switch 63 is rotated to the left, the rotary prism 41 is rotated to increase the prism power in an outward direction. In this manner, the prism power of the rotary prism 41 can be placed under desired conditions (in a desired direction) by the controller 60 (the dial switch 63). Incidentally, a command signal for rotating the rotary prism 41 may be generated and transmitted not by the dial switch but by a normal key (button) switch.

Figure 4:
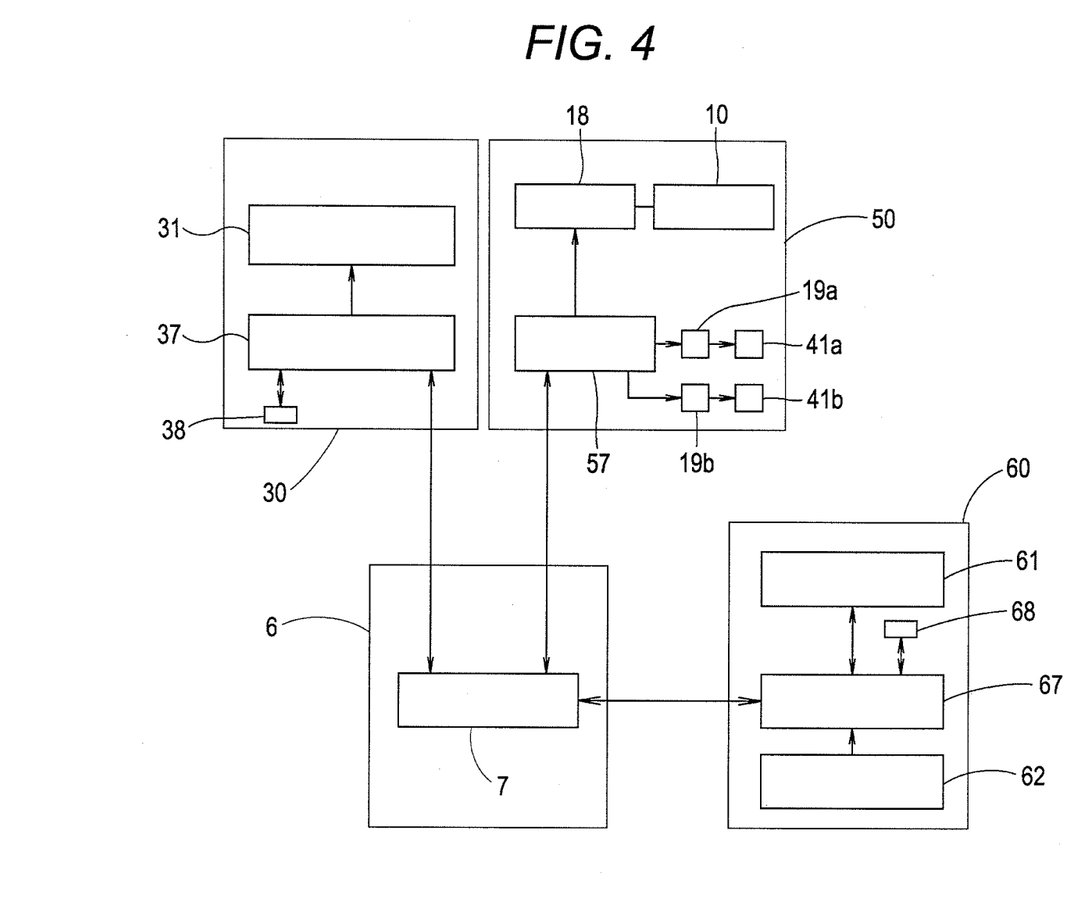
FIG. 4 is a schematic block diagram illustrating a control system of the optometric system.

Next, a description will be given of a control system of the optometric system 100. FIG. 4 is a schematic block diagram illustrating the control system of the optometric system 100. A control section (control unit) 7 for controlling the relay unit 6 is connected to a control section (control unit) 57 for controlling the optometric apparatus 50. The control section 7 is also connected to a control section (control unit) 37 for controlling the chart presenting apparatus 30. Furthermore, the control section 7 is connected to a control section (control unit) 67 for controlling the controller 60. The relay unit 6 is a unit for inputting and outputting data, command signals, and the like in the optometric system 100.

The control section 57 is connected to the motor 18 (the motors 18a to 18f), the motors 19a and 19b, and the like. The motor 18 (the motors 18a to 18f) is coupled to the group of lens disks 10 (the lens disks 11 to 16) via gears and the like (not shown). The motor 19a is coupled to the holder 42a (the prism 41a) via the gears 22 and 23 and the like. Furthermore, the motor 19b is coupled to the holder 42b (the prism 41b) via the gears 24 to 26 and the like. Incidentally, the control section 57 has a decoder and the like. The decoder decodes command signals transmitted from the controller 60 (the control section 67). These command signals include signals for driving the motors, disposing various types of optical elements in the test window 51, and the like.

The control section 37 is connected to the display 31, a memory 38 for storing (the data of) charts, and the like. The control section 37 has a decoder and the like. The decoder decodes command signals transmitted from the controller 60 (the control section 67).

The control section 67 is connected to the switch panel 62 including the monitor 61, the dial switch 63 and the like, and a memory 68 for storing test programs, test results and the like. In the embodiment, the controller 60 (the control section 67) supervises and controls the entire optometric system 100.

The command signals (command signals for switching the optical element, switching a chart, and the like) output from the monitor 61 and the switch panel 62 are transmitted from the control section 67 to the control section 7. The control section 7 allocates the received command signals to the control sections 57 and 37. The control section 57 drives the motors 18, 19a and 19b and the like based on the command signals. As a result, the optical element is disposed in the test window 51 (or the rotary prism 41 or the like rotates). The control section 37 reads (the data of) a chart from the memory 38 to display it on the display 31, in response to the command signal.

Figure 5:
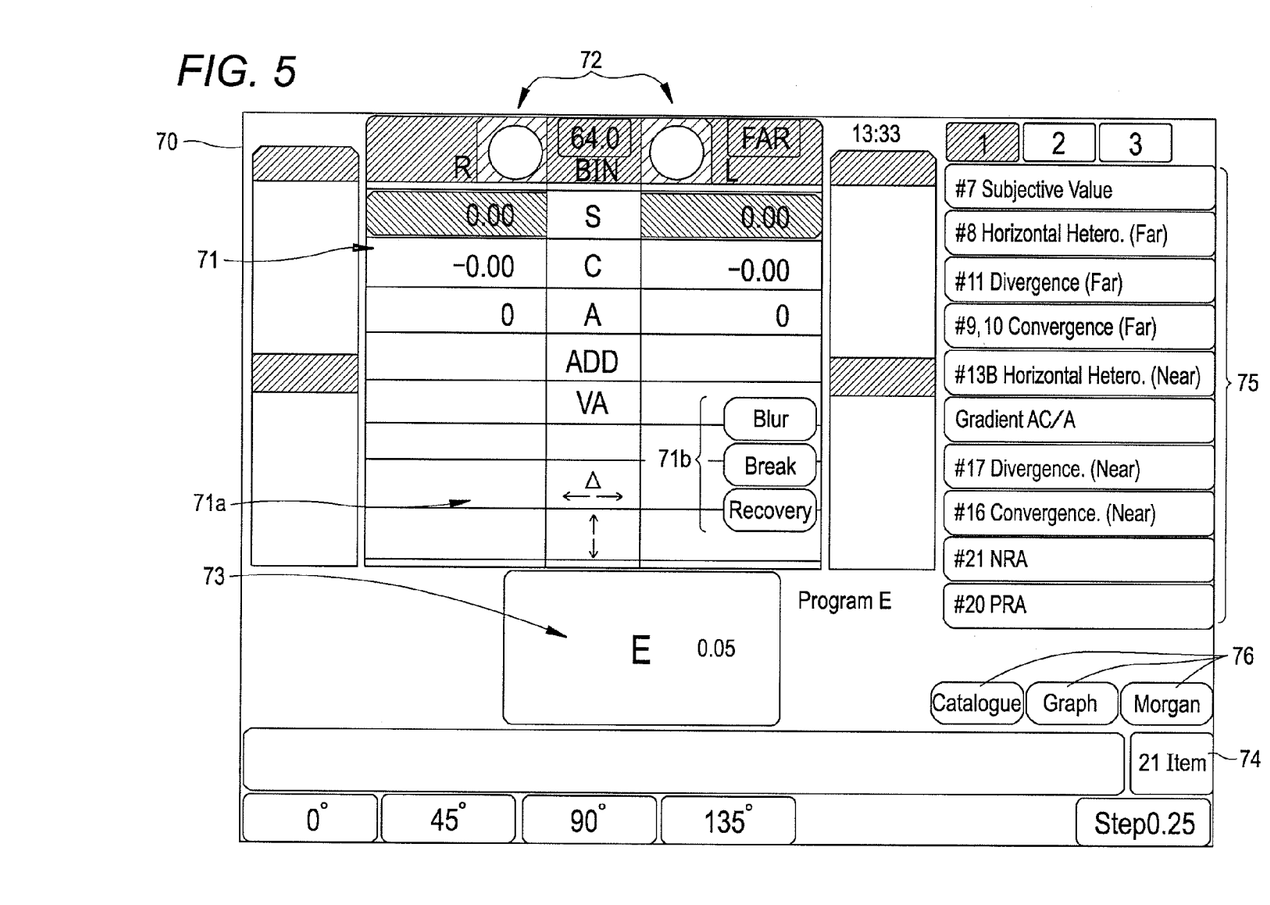
FIG. 5 is a view illustrating an exemplary screen displayed on a monitor upon a binocular visual function test.

Next, a description will be given of the operation of the optometric system 100 and a display screen of the monitor 61. Here, a description will be given of a display screen of when binocular visual function tests such as a phoria test are conducted after the perfect correction powers of the right and left eyes of the examinee are obtained. FIG. 5 is the display screen of the monitor 61 upon the binocular visual function test.

The examiner performs the following operations to obtain a perfect correction power. The right or left eye of the examinee is disposed in front of the corresponding test window 51 (the left test window 51L or the right test window 51R). The examiner causes the chart presenting apparatus 30 to present a distance visual acuity value test chart by operating the controller 60. With this, the examiner examines (measures) the spherical dioptic power and the like of the examinee's eye. Incidentally, the technology disclosed in JP-A-11-19041 (U.S. Pat. No. 6,048,064) can be used for a test procedure, a test method and the like for obtaining the perfect correction power of the examinee's eye.

A test information display screen 70 is displayed on the monitor 6L The screen 70 includes an examinee's eye information display unit 71, an auxiliary lens display unit 72, a chart display unit 73, a test selection switch 74, a test item display unit 75, a display changeover switch 76, and the like.

Information such as on the lens chamber unit 52 (the optical element disposed in the test window 51) and on the refractive power (degree of refraction) of the examinee's eye input after being obtained from another apparatus and the like is displayed on the display unit 71. Numerical values of the perfectly corrected degrees of refraction (the spherical dioptic power S, the astigmatic power C, the astigmatic axial angle A, and the like) are displayed on the display unit 71. Moreover, the display unit 71 has a prism power display unit 71a for displaying and inputting a prism power A. Furthermore, the display unit 71a has a classification display unit 71b for inputting and displaying a prism power while classifying the prism power by kind upon a divergence test, a convergence test and the like. The auxiliary lens disposed in the test window 51 (the left test window 51L and the right test window 51R) is displayed on the display unit 72. A selected chart (that is displayed on the display 31) is displayed on the display unit 73.

The words related to the binocular visual function tests are displayed on the switch 74 in order for the examiner to recognize it easily. In the example of FIG. 5, the words related to the 21-Point Examination are displayed. The test items of a test selected by the switch 74 are displayed in list form on the display unit 75. In the example of the drawing, the test items of the 21-Point Examination are displayed while lining up in the order of general frequency of use. Page transition tabs are provided in an upper part of the display unit 75. The test items that cannot be displayed on the display unit 75 are displayed on and after the next page. The switch 76 is a switch for displaying (outputting) the list of test results and displaying (outputting) an analysis results based on the test results. The analysis in the embodiment includes two processes: one is of displaying prism powers corresponding to the visual functions (the amount of phoria, the power of divergence, and the power of convergence) of the examinee as a visual function analysis graph that is easy to understand visually; and the other is of Morgan's analysis based on the test results (a comparison with Morgan's normative values).

If the test item is selected on the display unit 75, the control section 67 transmits a command signal to the control section 57 based on a selection signal. As a result, the auxiliary lens and the like are disposed in the test window 51 (the left test window 51L and the right test window 51R). In addition, the control section 67 changes an input status of the switch panel 62. For example, if a horizontal phoria test is selected, the control section 67 receives the rotation of the dial switch 63 as input of an increase and decrease in prism power.

Furthermore, if a far test is selected on the display unit 75, the control section 67 transmits a command signal to the control section 37 based on a selection signal. As a result, (the data of) a chart is read from the memory 38, and is displayed on the display 31.

Furthermore, if a near test is selected on the display unit 75, the control section 67 transmits a command signal to the control section 37 based on a selection signal. As a result, the display on the display 31 is blanked (or the whole screen whitens). The examiner then disposes the chart presenting unit 55 in front of the examinee. The examinee manually operates the chart presenting unit 55 to select a chart, move the chart (set a test distance), and the like.

In the embodiment, the following six items are examined from among the 21-Point Examination. A visual function analysis graph is subsequently created based on the test results, and is displayed. In the following tests, the numerals in parentheses indicate the serial numbers of the 21-Point Examination. The test items are: a far horizontal phoria test (#8), a far divergence test (a negative relative vergence test) (#11), a far convergence test (a positive relative vergence test) (#9 and #10), a near phoria test (#13B), a near divergence test (#17), and a near convergence test (#16) in order of testing. Such an order of testing is determined considering a burden on the examinee, the efficiency in testing, and the like. Incidentally, summaries of the tests are indicated in the specification. The detailed descriptions of the tests are disclosed in JP-A-11-19041.

The dispersion prisms are disposed in the test window 51 (the left test window 51L and the right test window 51R) in the far horizontal phoria test and the near horizontal phoria test (two items). A vertical line chart is broken apart by the prisms. Furthermore, the rotary prisms 41 are disposed in the test window 51 (the left test window 51L and the right test window 51R). The examiner rotates the dial switch 63 (in other words, rotates the rotary prism 41) while checking whether the examinee can see, in a vertical line, the charts that can be seen by the right and left eyes of the examinee. As a result, the prism power to be added to the examinee's eyes is changed (adjusted). The prism power of when the examinee can see the charts in a vertical line is the amount of phoria of the examinee.

The rotary prisms 41 are disposed in the test window 51 (the left test window 51L and the right test window 51R) in the far divergence test, the far convergence test, the near divergence test, the near convergence test (four items) (the vertical line chart is used similarly to the horizontal phoria test). The examiner asks the examinee to check how he/she sees the chart while rotating the dial switch 63 (rotating the rotary prism 41). In this manner, the examiner changes (adjusts) the prism power to be added to the examinee's eye. Additionally, the prism powers of when the examinee sees the chart blurrily (at the time of blur), sees the chart break apart (at the time of break), and sees the chart recover (sees the chart as one vertical line again) (at the time of recovery) are obtained. In the divergence test, the prism power is increased to incline the line of sight inwardly (in the base in direction). As a result, the power of divergence (the fusional amplitude) of the examinee is obtained (measured). In the convergence test, the prism power is increased to incline the line of sight outwardly (in the base out direction). As a result, the power of convergence (the fusional amplitude) of the examinee is obtained (measured).

Incidentally, the vertical line chart is used for any of the far and near tests in the embodiment. The vertical line chart is a chart where numerals, letters and the like corresponding to a visual acuity value of any one of 0.7 and 1.0 line up in a vertical line.

The (data of the) prism powers obtained in this manner are stored in the memory 68 in the following procedure. In the phoria test, the control section 67 associates the state of the rotary prism 41 of when the display unit 71a is pressed with the prism power and direction obtained in the phoria test. Then, the control section 67 stores them in the memory 68. In the divergence and convergence tests, if any of the classification items ("blur", "break" or "recovery") of the display unit 71b is pressed, the control section 67 associates the prism power and direction (the condition of the rotary prism 41) at that time with the test item and the classification item, and stores them in the memory 68.

Figure 6:
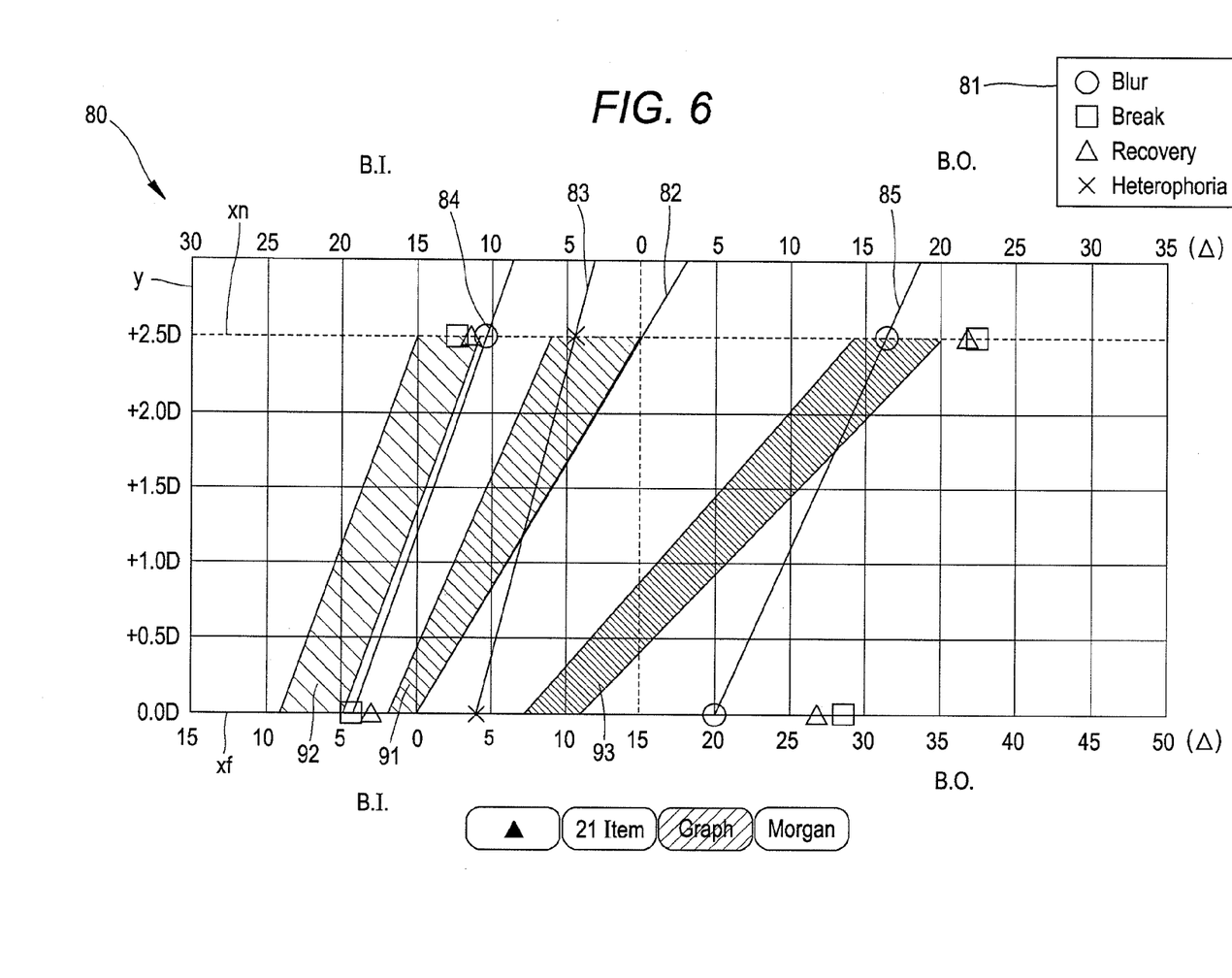
FIG. 6 is a view illustrating an exemplary screen on which a visual function analysis graph is displayed.

Next, a description will be given of a visual function analysis graph. When the switch 76 is pressed after the phoria test and the like end and the test results are obtained, a graph display screen 80 depicted in FIG. 6 is displayed on the monitor 61. The control section 67 creates a visual function analysis graph based on a command signal from the switch 76, and displays the graph on the monitor 61. At this time, the control section 67 reads the (data of the) prism powers corresponding to the test results of the examinee's eye from the memory 68 and performs the computation.

The screen 80 displayed on the monitor 61 includes lateral axes xf and xn, a longitudinal axis y, a Donders' line 82, a phoria line 83, an RCI (Relative Convergence Inhibitory) line 84, and an RCS (Relative Convergence Stimulatory) line 85 as a graph. Additionally, normative areas 91, 92, and 93 superimposed and displayed on the graph are included in the screen 80.

The lateral axes xf and xn represent the amount of a change in the eye position as the prism power Δ on the screen 80. The longitudinal axis y represents an accommodative stimulus. In other words, the longitudinal axis y designates the reciprocal of a test distance in diopter (D). In the embodiment, the far test distance (5 m) is set to be an infinite distance (0 D, no accommodative stimulus). Therefore, the lateral axis xf for the far test becomes an x coordinate of when the longitudinal axis y is 0 D. Additionally, the near test distance is set at 40 cm. Therefore, the lateral axis xn for the near test becomes an x coordinate of when the longitudinal axis y is 2.5 D (1/0.4 m).

A leftward direction from the symbols ○ and Δ is defined as a base in (BI) direction (divergence (negative relative vergence) direction) on the lateral axes xf and xn. On the other hand, a rightward direction from the symbols ○ and Δ is defined as a base out (BO) direction (convergence (positive relative vergence) direction). Incidentally, the pupillary distance PD is set at the norm of 60 mm in the graph. Therefore, convergence (positive relative vergence) of 15 Δ (60 mm/40 cm) occurs at the near test distance of 40 cm. Consequently, reference points on the lateral axes deviate by 15 Δ between the far and near tests. Hence, the reference point on the lateral axis xn for the near test (the reference point of when a phoria is not present) becomes 15 Δ (the reference point on the lateral axis xf for the far test becomes 0 D).

A case display unit 81 on the screen 80 shows four different marks indicating the break of the prism powers obtained in the tests. These marks are "○" showing the prism power at the time of blur, "□" showing the prism power at the time of break, "Δ" showing the prism power at the time of recovery, and "×" showing the prism power corresponding to the amount of phoria. The (data of the) prism powers corresponding to the tests, which are stored in the memory 68, are plotted on the lateral axes xf and xn with the corresponding marks. Moreover, straight lines (line segments) formed by connecting the same types of marks plotted on the axes xf and xn with each other are also displayed on the screen 80.

The Donders' line 82 is a straight line showing accommodative stimulus and convergence stimulus for seeing the chart clearly as one at a near test distance and a far test distance. The Donders' line 82 is a straight line passing through the reference point of the near test and the reference point of the far test for handling an eye position with no phoria. In other words, the Donders' line 82 is a straight line having a certain relationship. Incidentally, the inclination of the Donders' line 82 indicates an ideal eye position. The inclination is a reference of when the amount of phoria and the like of the examinee are displayed on a graph.

The phoria line 83 is a straight line connecting a prism power corresponding to the amount of phoria obtained by the far test and a prism power corresponding to the amount of phoria obtained by the near test. The tendency of the phoria of the examinee can be recognized from the inclination of the phoria line 83.

The RCI line 84 is a straight line connecting a prism power at the time of break (not at the time of blur) obtained by the far divergence test and a prism power at the time of blur obtained by the near divergence test. The RCI line 84 represents the power of divergence of the examinee. The characteristic of divergence of the examinee can be obtained from the inclination of the RCI line 84.

The RCS line 85 is a straight line connecting a prism power at the time of blur obtained by the far convergence test and a prism power at the time of blur obtained by the near convergence test. The RCS line 85 represents the power of convergence of the examinee. The convergence characteristics of the examinee can be recognized from the inclination of the RCS line 85.

In this manner, the eye position of the examinee can be easily recognized by comparing the inclinations and positions of the phoria line 83, the RCI line 84 and the RCS line 85 with the inclination and position of the Donders' line 82.

Incidentally, the marks with larger prism powers than the RCS line 85 ("□" and "Δ" in FIG. 6) are ignored when the RCS line 85 is drawn.

The normative area (phoria normative area) 91 displayed on the screen 80 is an area of a normative (no abnormal) prism power in the phoria test. The maximum and minimum values of a prism power obtained by the far test and the maximum and minimum values of a prism power obtained by the near test, which are within a normative range of the amount of phoria obtained by Morgan's analysis are plotted in the embodiment. An area enclosed with four plotted points is displayed in color. The area 91 is displayed in a pale color different from those of the straight lines, which does not prevent (block) the visibility of the straight lines such as the phoria line 83.

The normative area (divergence normative area) 92 displayed on the screen 80 is an area of a normative (no abnormal) prism power in the divergence test. The maximum and minimum values of a prism power obtained by the far test and the maximum and minimum values of a prism power obtained by the near test, which are within a normative range of the power of divergence obtained by Morgan's analysis are plotted in the embodiment. An area enclosed with four plotted points is displayed in color. The display color of the area 92 may be different from the display color of the area 91 to differentiate it easily. Moreover, the area 92 is displayed in a pale color different from those of the straight lines, which does not prevent the visibility of the straight lines.

The normative area (convergence normative area) 93 displayed on the screen 80 is an area of a normative (no abnormal) prism power in the convergence test. The maximum and minimum values of a prism power obtained by the far test and the maximum and minimum values of a prism power obtained by the near test, which are within a normative range of the power of convergence obtained by Morgan's analysis are plotted in the embodiment. An area enclosed with four plotted points is displayed in color. The display color of the area 93 may be different from the display colors of the areas 91 and 92 to differentiate it easily. Moreover, the area 93 is displayed in a pale color different from those of the straight lines, which does not prevent the visibility of the straight lines.

Representation of the areas 91 to 93 on the graph allow the examiner to visually recognize the inclinations of the normative eye position and the powers of divergence and convergence, and the amplitude of the prism power. Furthermore, the straight lines (such as the phoria line 83) representing the characteristics of phoria and the like of the examinee and the areas 91 to 93 are displayed on the same screen. Therefore, it is easy to grasp how different the amount of phoria, the powers of divergence and convergence, and the like of the examinee are from the norms. Moreover, the areas 91 to 93 are displayed in different colors to differentiate themselves. Therefore, it is easy to understand what characteristics the straight lines represent. For example, if there is a straight line near the area 92, the straight line can be easily recognized as the RCI line 84 representing the power of divergence.

As is evident from the example of the graph displayed on the screen 80, the example being depicted in FIG. 6, the amount of phoria obtained by the far test has a slight tendency of esophoria. On the other hand, the amount of phoria obtained by the near test is found to be normative. Moreover, it is found that the power of divergence has a normative inclination and does not change largely by accommodation. Furthermore, it is found that the power of divergence is slightly smaller than the norm (is close to the reference point). On the other hand, it is found that the power of convergence obtained by the far test is larger than the norm, but the power of convergence obtained by the near test is normative.

If the amount of phoria and the power of convergence are inclined more largely than the norms, there are few changes by the spherical adjustments. In contrast, the amount of phoria and the power of convergence, which have smaller inclinations than the norms, are susceptible to the influence of the spherical adjustments. In the example of FIG. 6, the inclinations of the phoria line 83 and the RCS line 85 are larger than the inclination of the norms (the areas 91 and 93). Therefore, a prism prescription can be determined as one more effective than a spherical adjustment (prism prescription can be estimated more effectively).

In this manner, the optometric apparatus 50 displays the test results (prism powers) of the tests in straight lines while displaying areas corresponding to the normative ranges of the test results. Consequently, the analysis results of the binocular visual function tests such as the phoria test can be easily recognized. Furthermore, an appropriate prescription value can be obtained efficiently and easily.

Incidentally, the normative areas 91 to 93 may not be displayed in color. For example, the normative areas 91 to 93 may be hatched. Moreover, multiple straight lines may be displayed in the normative areas 91 to 93. In other words, it is sufficient if the normative areas 91 to 93 are displayed appropriately so as to differentiate them from the other parts. Additionally, it may be possible to switch the normative areas between visible and not visible.

Moreover, in the above description, the prism powers corresponding to the distances between the distance for the far test (0 D) and the distance for the near test (2.5 D) are graphed. However, it is not necessarily limited to this, and the straight lines such as the phoria line may be extended to a range corresponding to a test distance shorter than 2.5 D. The extension of the straight lines makes it possible to estimate the amount of phoria and the like to some extent.

Furthermore, in the above description, the straight lines related to the amount of phoria, and the powers of divergence and convergence are displayed on one graph. However, it is not necessarily limited to this, and the straight lines may be displayed on separate graphs. Additionally, the tests for the amount of phoria and the powers of divergence and convergence are not limited to horizontal direction tests. Moreover, the prism powers displayed on a graph are not limited to those that can be obtained by the horizontal direction tests.

Furthermore, in the above description, the graph representing the test results (the prism powers) are displayed on the monitor. However, it is not necessarily limited to this. The test results may be output in a manner easy to be grasped visually. For example, the graph showing the test results may be output to an external storage device as image data and may be printed by use of a printer and the like.

Moreover, in the above description, the normative areas of the amount of phoria and the like are set by plotting the numerical values within normative ranges of prism powers obtained by Morgan's analysis. However, it is not necessarily limited to this, and the normative numerical ranges used for the setting of the normative areas may be ranges corresponding to an analysis (statistical result) different from Morgan's analysis. Furthermore, the user (examiner) may define the numerical ranges.

Moreover, in the above description, the optometric apparatus 50 obtains the prism powers corresponding to the amount of phoria and the powers of divergence and convergence of the examinees' eye while computing them to create and display (output) a graph. However, it is not necessarily limited to this, and the prism powers of the examinees' eye may be input into a computer that executes the computation and output processing. The computer for this processing may be a general-purpose computer including: a microprocessing unit for supervising and controlling the computer; an input unit for inputting data such as the prism powers of the examinee's eye; a memory for storing data such as prism powers, processing programs, and the like; output units such as a monitor and a printer; and operation units such as a mouse and a keyboard.

Furthermore, the optometric apparatus in the embodiment can also be represented as following first to seventh optometric apparatuses.

In other words, a first optometric apparatus is an optometric apparatus for conducting an examination to obtain a prescription value for the visual dysfunction of an examinee's eye, including: a memory, an output unit, and a control unit. The memory is provided for storing prism powers added to the examinee's eye. The output unit is provided for outputting test results. The control unit is provided for graphically outputting to the output unit information on prism powers of the examinee's eye based on the prism powers stored in the memory while graphically outputting to the output unit normative areas showing areas of normative prism powers as well as the information on the prism powers output graphically.

A second optometric apparatus is the first optometric apparatus including: a rotary prism for adding a prism power to the examinee's eye; and an operation unit for transmitting a command signal for rotating the rotary prism to allow the rotary prism to add a desired prism power to the examinee's eye.

A third optometric apparatus is the first optometric apparatus in which the information on the prism powers has a horizontal phoria test, a divergence test, and a convergence test.

A fourth optometric apparatus is the first optometric apparatus in which the information on the prism powers has a far test and a near test.

A fifth optometric apparatus is the first optometric apparatus in which the normative areas are displayed in a manner of not blocking display of the information on the prism powers.

A sixth optometric apparatus is the first optometric apparatus in which the normative areas are displayed in display colors different from display colors of the information on the prism powers. According to these first to sixth optometric apparatuses, analysis results of binocular visual function tests such as a phoria test can be easily recognized. In addition, an appropriate prescription value can be easily obtained.

A seventh optometric apparatus includes an examination unit, an output unit, and a control unit. The examination unit is provided for examining prism powers corresponding to visual functions of an examinee's eye. The output unit is provided for displaying information on prism powers of the examinee's eye based on the prism powers obtained by the examination unit, and normative areas being areas of normative prism powers. The control unit is provided for controlling the examination by the examination unit and the display by the output unit. The examination unit has the pair of lens chamber units 52, the support unit 53, the chart presenting unit (near test chart presenting unit) 55, the near-point rod 56, and the controller 60 in the optometric system 100 illustrated in FIG. 1, for example.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. An optometric apparatus for examining visual functions of an examinee's eye, comprising:
   a memory for storing prism powers corresponding to the visual functions of the examinee's eye, the memory configured to store a first prism power of the examinee's eye obtained through a horizontal phoria test, a second prism power of the examinee's eye obtained through a divergence test, and a third prism power of the examinee's eye obtained through a convergence test;
   an output unit; and
   a control unit for graphically displaying on the output unit a first normative area of an area of a normative prism power in the horizontal phoria test, a second normative area being an area of a normative prism power in the divergence test, and a third normative area being an area of a normative prism power in the convergence test, in addition to information on the first prism power of the examinee's eye based on the first prism power, information on the second prism power of the examinee's eye based on the second prism power, and information on the third prism power of the examinee's eye based on the third prism power, the first prism power, the second prism power, and the third prism power configured to be stored in the memory.

2. The optometric apparatus according to claim 1, comprising:
   a rotary prism for adding a prism power to the examinee's eye; and an operation unit for generating a command signal for rotating the rotary prism to allow the rotary prism to add a desired prism power to the examinee's eye.

3. The optometric apparatus according to claim 1, wherein the information on the first prism power, the second prism power, and the third prism power includes results of a far test and a near test.

4. The optometric apparatus according to claim 1, wherein the first normative area, the second normative area, and the third normative area are configured to be displayed so as to be distinguished from the information on the first prism power, the second prism power, and the third prism power.

5. The optometric apparatus according to claim 1, wherein display colors of the first normative area, the second normative area, and the third normative area are different from display colors of the information on the first prism power, the second prism power, and the third prism power.

6. The optometric apparatus according to claim 1, wherein
the information on the first prism power, the second prism power, and the third prism power each includes results of a far test and a near test,
the first normative area includes maximum and minimum values of a normative prism power in a far test of horizontal phoria, and maximum and minimum values of a normative prism power in a near test of horizontal phoria,
the second normative area includes maximum and minimum values of a normative prism power in a far test of divergence, and maximum and minimum values of a normative prism power in a near test of divergence, and
the third normative area includes maximum and minimum values of a normative prism power in a far test of convergence, and maximum and minimum values of a normative prism power in a near test of convergence.

7. The optometric apparatus according to claim 6, wherein
the control unit is configured to plot the maximum and minimum values in the far test of horizontal phoria and the maximum and minimum values in the near test of horizontal phoria, and graphically display, on the output unit, an area enclosed with four plotted points as the first normative area,
the control unit is further configured to plot the maximum and minimum values in the far test of divergence and the maximum and minimum values in the near test of divergence, and graphically display, on the output unit, an area enclosed with four plotted points as the second normative area, and
the control unit is further configured to plot the maximum and minimum values in the far test of convergence and the maximum and minimum values in the near test of convergence, and graphically display, on the output unit, an area enclosed with four plotted points as the third normative area.

8. An optometric apparatus for examining visual functions of an examinee's eye, comprising:
a memory for storing a prism power corresponding to at least one of the visual functions among horizontal phoria, divergence, and convergence, of the examinee's eye, the memory configured to store a far prism power in a far test of the at least one visual functions and a near prism power in a near test of the at least one visual functions;
an output unit; and
a control unit for graphically displaying on the output unit normative areas being areas of normative prism powers of the at least one visual functions in addition to information on the far prism power based on the far prism power of the examinee's eye and information on the near prism power based on the near prism power of the examinee's eye, the far prism power and the near prism power configured to be stored in the memory,
wherein the normative areas include areas of maximum and minimum values of a normative prism power in the far test and areas of maximum and minimum values of a normative prism power in the near test.

9. The optometric apparatus according to claim 1, further comprising:
a chart presenting unit configured to present a test chart for a far test; and
a relay unit configured to transfer command signals from the control unit to the chart presenting unit.

10. The optometric apparatus according to claim 1, further comprising:
at least one lens disk housing a plurality of lenses; and
a motor configured to move the at least one lens disk in response to a control signal generated by the control unit.

11. The optometric apparatus according to claim 1, further comprising:
a rotatable prism configured to be positioned in front of the examinee's eye; and
a motor configured to rotate the rotatable prism in response to command signals from the control unit.

12. The optometric apparatus according to claim 1, further comprising:
a chart presenting unit configured to present a test chart for a far test; and
at least one lens disk housing a plurality of lenses,
wherein the control unit further comprises a plurality of switches configured to receive instructions, and the control unit is configured to generate command signals to control the chart presenting unit and the at least one lens disk.

13. The optometric apparatus according to claim 8, further comprising:
a chart presenting unit configured to present a test chart for a far test; and
a relay unit configured to transfer command signals from the control unit to the chart presenting unit.

14. The optometric apparatus according to claim 8, further comprising:
at least one lens disk housing a plurality of lenses; and
a motor configured to move the at least one lens disk in response to a control signal generated by the control unit.

15. The optometric apparatus according to 8, further comprising:
a rotatable prism configured to be positioned in front of the examinee's eye; and
a motor configured to rotate the rotatable prism in response to command signals from the control unit.

16. The optometric apparatus according to claim 8, further comprising:
a chart presenting unit configured to present a test chart for a far test; and
at least one lens disk housing a plurality of lenses,
wherein the control unit further comprises a plurality of switches configured to receive instructions, and the control unit is configured to generate command signals to control the chart presenting unit and the at least one lens disk.

* * * * *